(12) United States Patent
Carver et al.

(10) Patent No.: US 6,770,670 B2
(45) Date of Patent: Aug. 3, 2004

(54) INJECTABLE COMPOSITION

(75) Inventors: David Carver, Boulder, CO (US); Timothy Prout, Erie, CO (US); Hernita Ewald, Denver, CO (US); Robyn Elliott, Lanowarrin (AU); Paul Handreck, Glen Iris (AU)

(73) Assignee: NaPro BioTherapeutics, Inc., Boulder, CO (US)

( * ) Notice: Subject to any disclaimer, the term of this patent is extended or adjusted under 35 U.S.C. 154(b) by 67 days.

(21) Appl. No.: 09/970,558

(22) Filed: Oct. 4, 2001

(65) Prior Publication Data

US 2003/0065022 A1 Apr. 3, 2003

Related U.S. Application Data

(63) Continuation of application No. 09/563,969, filed on May 3, 2000, now Pat. No. 6,306,894, which is a continuation of application No. 09/356,158, filed on Jul. 19, 1999, now Pat. No. 6,140,359, which is a continuation of application No. 08/979,836, filed on Nov. 26, 1997, now Pat. No. 5,977,164, which is a division of application No. 08/594,478, filed on Jan. 31, 1996, now Pat. No. 5,733,888, which is a continuation of application No. 07/995,501, filed on Dec. 22, 1992, now abandoned.

(30) Foreign Application Priority Data

Nov. 27, 1992 (AU) .................................................. 6074

(51) Int. Cl.⁷ ............................................. A61K 31/335
(52) U.S. Cl. ................................................... 514/449
(58) Field of Search ........................................ 514/449

(56) References Cited

PUBLICATIONS

Richheimer, 1991, "High Performance Liquid Chromatographic Assay of Taxol", Anal. Chem., Oct. 1992, vol. 64, which is disclosed in Professor's Blechert's Israeli Declaration filed in the Israel Opposition to related application.*
Sep. 1983, National Cancer Institute Report for Taxol NSC 125973.*
Roger W. Miller et al., Antileukemic Alkaloids from *Taxus wallichiana* Zucc., J. Org. Chem, 1981, 46:1469–1474.
National Cancer Institute. Division of Cancer Treatment, Bethesda, Maryland, Clinical Brochure, Taxol IND 22850. NSC 125973, Jul. 1991, pp. 1–36.
Abraham E. Mathew et al., Synthesis and Evaluation of Some Water–Soluble Prodrugs and Derivatives of Taxol with Antitumor Activity, J. Med. Chem., 1992, 35:145–151.
J.R. Kagel et al., Taxol Stability in Aqueous Solutions or in Organic/Aqueous Cosolvents, 8ᵗʰ AAPS National Meeting, Orlando, FL, Nov. 14–18, 1993.
National Cancer Institute, Division of Cancer Treatment, Bethesda, Maryland, Clinical Brochure, Taxol NSC 125973, Sep. 1983, pp. 1–54.
Professor Blechert's Israeli Declaration filed in the Israel Opposition to a related application, and also made of record in the European Opposition.

Susan G. Arbuck et al., A Reassessment of Cardiac Toxicity Associated with Taxol, Journal of the National Cancer Institute Monographs, 1993, 15:117–130.
K. Reber, Inhibition of Haemolysis by 'Cremophor' in Conserved Blood, Nature, Oct. 9, 1965, 208(5006):195.
Taxol Brochure, MeadJohnson Oncology Products, A Bristol–Myers Squibb Company, Jul. 2000, 6 pages.
National Cancer Institute, Division of Cancer Treatment, Bethesda, Maryland, Annual Report to the Food and Drug Administration, Taxol IND 22850 NSC 125573, Feb. 1989, pp. 1–25.
English language translation of informal signed statement from Professor Blechert attesting to various pH determinations which he purported he had carried out, Jun. 2002.
Decision issued by the European Patent Office revoking European Patent No. 0674510.
Consolidated Document List cited all reference documents relied on during prosecution of the Appeal process of European Patent No. 0674510.
NaPro Biotherapeutics, Inc. and Abbott Laboratories v. Mylan Laboratories, Inc., Mylan Pharmaceuticals, Inc. and UDL Laboratories, Inc., Civil Action No. 01–CV–1048 (W.D. PA), Stipulation and Protective Order.
NaPro Biotherapeutics, et al. v. Mylan Laboratories, et al., Case No. 01–CV–1048 (W.D. PA), Patent Infringement, litigation, court docket.
NaPro Biotherapeutics, Inc., et al. v. Bristol–Myers Squibb Co., Case No. 00–CV–1818 (D. CO), Patent Infringement, litigation, court docket.
NaPro Biotherapeutics, Inc. and Abbott Laboratories v. Mylan Laboratories, Inc., Mylan Pharmaceuticals, Inc. and UDL Laboratories, Inc., Civil Action No. 01–CV–1048 (W.D. PA), Amended Answer and Counterclaims of Defendants to Second Amended Complaint.
NaPro Biotherapeutics, Inc. and Abbott Laboratories v. Bristol–Myers Squibb Co., Civil Action No. 00–B–1818 (D. CO), Defendant's Responses and Objections to Plaintiffs' First Set of Interrogatories.

(List continued on next page.)

*Primary Examiner*—Dwayne C. Jones
(74) *Attorney, Agent, or Firm*—Saliwanchik, Lloyd & Saliwanchik

(57) ABSTRACT

A pharmaceutical formulation of paclitaxel and polyethoxylated castor oil is disclosed to be relatively acidified to a pH of less than 8.1 and preferably within a pH range of 5 to 7, inclusively. Ethanol is optionally included in the formulation which is adapted for use in a body for the treatment of cancer, A formulation method is disclosed and includes the step of mixing an acid with a carrier material, such as polyethoxylated castor oil, to form a carrier solution after which paclitaxel is added in an amount such that the resulting pH is less than 8.1 and preferably in a pH range of 5 to 7. Ethanol may optionally be slurried with the paclitaxel before mixing with the carrier solution. A variety of acidifying agents, a preferred one being anhydrous citric acid, are described.

265 Claims, No Drawings

PUBLICATIONS

NaPro Biotherapeutics, Inc. and Abbott Laboratories v. Bristol–Myers Squibb Co., Civil Action No. 00–B–1818 (D. CO), Defendant's Answer to First Amended Complaint. Information Disclosure Statement dated Nov. 26, 1996 filed in parent application USSN 08/594,478, now U.S. patent No. 5,733,888.

Opponent's Reponse to the Appeal dated Sep. 12, 2003 in the EPO, along with copies of references cited therein.

Second Affidavit of Prof. Siegfried Blechert; opinion concerning related Israeli patent in support of the opposition filed by Teva Pharmaceuticals Industries Ltd.

* cited by examiner

INJECTABLE COMPOSITION

CROSS-REFERENCE TO RELATED APPLICATIONS

This application is a continuation of U.S. Ser. No. 09/563,969, filed May 3, 2000, now U.S. Pat. No. 6,306,894; which is a continuation of U.S. Ser. No. 09/356,158, filed Jul. 19, 1999, now U.S. Pat. No. 6,140,359; which is a continuation of U.S. Ser. No. 08/979,836, filed Nov. 26, 1997, now U.S. Pat. No. 5,977,164; which is a divisional of U.S. Ser. No. 08/594,478, filed Jan. 31, 1996, now U.S. Pat. No. 5,733,888; which is a continuation of U.S. Ser. No. 07/995,501, filed Dec. 22, 1992, now abandoned.

CROSS-REFERENCE TO RELATED FOREIGN APPLICATION

This application claims priority under 35 U.S.C. 119 to Australian Patent No. 6074, filed Nov. 27, 1992.

This invention relates to a solution of paclitaxel having improved stability.

BACKGROUND OF THE INVENTION

Paclitaxel is a compound extracted from the bark of a western yew, *Taxus brevifolia* and known for its antineoplastic activity. It is described for example in The Merck Index, Eleventh Edition 1989, monograph 9049.

In 1977, paclitaxel was chosen for development as an antineoplastic agent because of its unique mechanism of action and good cytotoxic activity against IP implanted D16 melanoma and the human X-1 mammary tumor xenograft. Paclitaxel is believed to function as a mitotic spindle poison and as a potent inhibitor of cell replication in vitro. Other mitotic spindle points (colchicine and podophyllotoxin) inhibit microtubule assembly. Paclitaxel employs a different mechanism of action since it appears to shift the equilibrium of polymerization/depolymerization toward polymer assembly and to stabilize microtubules against depolymerization under conditions which would cause rapid disaggregation of microtubules. The interference with the polymerization/depolymerization cycle in cells appears to interfere with both the replication and migration of cells.

After extensive preclinical screening in mouse tumor models, paclitaxel entered clinical trials in 1983. Over the past few years, paclitaxel has demonstrated good response rates in treating both ovarian and breast cancer patients who were not benefitting from vinca alkaloid or cisplatin therapy. It has also shown encouraging results in patients with other types of cancer including lung, melanoma, lymphoma, head and neck.

For further information, reference may be made to the U.S. National Cancer Institute's Clinical Brochure for Taxol, revised July 1991, and papers presented at the Second National Cancer Institute Workshop on Taxol and Taxus held in Alexandria, Va. USA on Sep. 23–24, 1992.

BRIEF DESCRIPTION OF THE INVENTION

It is a disadvantage of the known formulation that the paclitaxel therein degrades, with the result that the shelf life of the formulation is unsatisfactory, and there is therefore a need for a paclitaxel solution of improved stability.

Accordingly, in a general aspect the invention provides a solution containing paclitaxel, cremophor EL™ and ethanol, characterized in that the pH of the solution has been adjusted into the range 1 to 8 by addition of an acid.

Acids in the form of powders, for example citric acid, are preferred over those which contain water, for example sulfuric acid. The most preferred acid for use in accordance with the present invention is citric acid, but a wide range of acids may be used including the following:

Citric acid—monohydrous
Citric acid—anhydrous
Citric acid—hydrous
Acetic acid
Formic acid
Ascorbic acid
Aspartic acid
Benzene sulphonic acid
Benzoic acid
Hydrochloric acid
Sulphuric acid
Phosphoric acid
Nitric acid
Tartaric acid
Diatrizoic acid
Glutamic acid
Lactic acid
Maleic acid
Succinic acid

DETAILED DESCRIPTION OF THE ILLUSTRATED EMBODIMENTS

Due to its limited solubility in water, Paclitaxel is usually prepared and administered in a vehicle containing cremophor EL™ (a polyethoxylated castor oil which acts as a solubilizer) and ethanol. A commercially available solution supplied by Bristol-Myers Squibb (BMS) is formulated with these components and has a pH of 9.1.

As indicated above, the invention essentially teaches addition of an acid to a paclitaxel formulation to adjust its pH into the range 1 to 8, preferable 5 to 7.

In a preferred procedure adopted by the applicant, which it will be clearly understood is non-limiting, the following steps were carried out:

Mixing Instructions
Solution 1
Citric acid was dissolved in absolute alcohol, using a ratio of 8 mls of absolute alcohol to 1 gram of citric acid, and the solution was stirred for fifteen (15) minutes.
Solution 2
Cremophor EL was weighed out into the main mixing vessel.
Solution 3
Solution 1 was added to solution 2, and the container used for solution 2 was washed with a minimum quantity of absolute alcohol to ensure complete transfer of the citric acid. Solution 3 was mixed and bubbled with nitrogen for at least 15 minutes. The paclitaxel was weighed out and slurried using absolute alcohol using a ratio of 8 ml of absolute alcohol to 1 gm of paclitaxel. The slurried paclitaxel was added to solution 3 and the slurrying vessel was washed with a minimum quantity of absolute alcohol. Solution 3 was adjusted to 75% of required volume using absolute alcohol and thoroughly stirred for at least 45 minutes until completely dissolved. Once completely dissolved, the volume was checked and made up as necessary with absolute alcohol and the final solution stirred for 5 minutes.

EXAMPLE 1

A solution was prepared with the following formulation:

| Formulation: (Sample 1) | |
| --- | --- |
| Cremophor EL | 0.5 mL |
| Citric Acid (Anhydrous) | 2.0 mg |
| Paclitaxel | 6.0 mg |
| Absolute Alcohol | to 1.0 mL |

The pH of this solution was determined as 6.1.

The stability of this sample was compared with a sample prepared by the formulation stated in the NCI Taxol Clinical brochure (as follows) which had a pH of 9.1. (Sample 2)

| Sample 2 | per mL |
| --- | --- |
| Paclitaxel | 6 mg |
| Cremophor EL | 0.5 mL |
| Absolute Alcohol | to 1 mL |

The solutions were filled into clear type 1 glass 5 mL vials and sealed with rubber bungs.

The solutions were stored at 40° C. for 7 (seven) days and the stability results are shown in Table 1.

| | Sample 1 | Sample 2 |
| --- | --- | --- |
| pH | 6.2 | 9.0 |
| Potency | 96.6 | 86.7 |
| Major individual impurity | 0.3% | 5.1% |
| Total impurities | 1.0% | 12.2% |

Clearly Sample 1 showed significantly increased stability over Sample 2.

EXAMPLE 2

A solution was prepared with the following formulation:

| Formulation: (Sample 3) | |
| --- | --- |
| Cremophor EL | 0.5 mL |
| Paclitaxel | 6.0 mg |
| Absolute Ethanol | to 1.0 mL | pH adjusted to 6.6 with 1.0M Acetic Acid.

The solution was filled into clear type I glass 5 mL vials and sealed with rubber bungs.

The solution was stored at 40° C. for 7 days.

The stability results obtained are compared to those seen with Sample 2.

| | Sample 3 | Sample 2 |
| --- | --- | --- |
| pH | 6.7 | 9.0 |
| Potency | 97.5 | 86.7 |
| Major individual impurity | 0.3% | 5.1% |
| Total impurities | 2.3% | 12.2% |

Again the significantly superior stability of the formulation according to the invention (Sample 3) is evident.

It will be clearly understood that the invention in its general aspects is not limited to the specific details referred to hereinabove.

What is claimed is:

1. A pharmaceutical paclitaxel composition comprising:
   paclitaxel;
   polyethoxylated castor oil; and
   an acid; said composition being such that at least 96.6% of the paclitaxel potency is retained when the composition is stored at 40° C. for seven days.

2. The pharmaceutical paclitaxel composition of claim 1, further comprising ethanol.

3. The pharmaceutical paclitaxel composition of claim 1, wherein said acid is an organic acid.

4. The pharmaceutical paclitaxel composition of claim 1, wherein said acid is a mineral acid.

5. The pharmaceutical paclitaxel composition of claim 3, wherein said acid is citric acid.

6. The pharmaceutical paclitaxel composition of claim 5, wherein said citric acid is monohydrous.

7. The pharmaceutical paclitaxel composition of claim 5, wherein the citric acid is hydrous.

8. The pharmaceutical paclitaxel composition of claim 5, wherein the citric acid is anhydrous.

9. The pharmaceutical paclitaxel composition of claim 3, wherein said acid is acetic acid.

10. The pharmaceutical paclitaxel composition of claim 2, wherein said acid is an organic acid.

11. The pharmaceutical paclitaxel composition of claim 2, wherein said acid is a mineral acid.

12. The pharmaceutical paclitaxel composition of claim 10, wherein said acid is citric acid.

13. The pharmaceutical paclitaxel composition of claim 10, wherein said citric acid is monohydrous.

14. The pharmaceutical paclitaxel composition of claim 10, wherein the citric acid is hydrous.

15. The pharmaceutical paclitaxel composition of claim 10, wherein the citric acid is anhydrous.

16. The pharmaceutical paclitaxel composition of claim 10, wherein said acid is acetic acid.

17. An article of manufacture comprising a sealed container and a pharmaceutical paclitaxel composition disposed within said sealed container, said pharmaceutical paclitaxel composition comprising:
    paclitaxel;
    a pharmaceutically-acceptable carrier; and
    an acid; said composition being such that at least 96.6% of the paclitaxel potency is retained when said composition is stored at 40° C. for seven days.

18. An article of manufacture of claim 17, wherein said pharmaceutically-acceptable carrier comprises polyethoxylated castor oil.

19. The article of manufacture of claim 18, wherein said pharmaceutically-acceptable carrier further comprises ethanol.

20. The article of manufacture of claim 17, wherein said acid is an organic acid.

21. The article of manufacture of claim 17, wherein said acid is a mineral acid.

22. The article of manufacture of claim 20, wherein said acid is acetic acid.

23. The article of manufacture of claim 20, wherein said acid is citric acid.

24. The article of manufacture of claim 23, wherein said citric acid is anhydrous.

25. The article of manufacture of claim 23, wherein said citric acid is monohydrous.

26. The article of manufacture of claim 23, wherein said citric acid is hydrous.

27. The article of manufacture of claim 18, wherein said acid is an organic acid.

28. The article of manufacture of claim 18, wherein said acid is a mineral acid.

29. The article of manufacture of claim 27, wherein said acid is acetic acid.

30. The article of manufacture of claim 27, wherein said acid is citric acid.

31. The article of manufacture of claim 30, wherein said citric acid is anhydrous.

32. The article of manufacture of claim 30, wherein said citric acid is monohydrous.

33. The article of manufacture of claim 30, wherein said citric acid is hydrous.

34. The article of manufacture of claim 19, wherein said acid is an organic acid.

35. The article of manufacture of claim 19, wherein said acid is a mineral acid.

36. The article of manufacture of claim 34, wherein said acid is acetic acid.

37. The article of manufacture of claim 34, wherein said acid is citric acid.

38. The article of manufacture of claim 37, wherein said citric acid is anhydrous.

39. The article of manufacture of claim 37, wherein said citric acid is monohydrous.

40. The article of manufacture of claim 37, wherein said citric acid is hydrous.

41. An article of manufacture produced by the process of:
(a) obtaining a sealable container;
(b) obtaining a pharmaceutical formulation comprising paclitaxel, a pharmaceutically-acceptable carrier, and an acid; said formulation being such that at least 96.6% of the paclitaxel potency is retained when the formulation is stored at 40° C. for seven days;
(c) placing said pharmaceutical formulation in said sealable container;
(d) sealing said sealable container; and
(e) storing said pharmaceutical formulation in said sealed container for at least seven days.

42. The article of manufacture of claim 41, wherein said pharmaceutically-acceptable carrier comprises polyethoxylated castor oil.

43. The article of manufacture of claim 42, wherein said pharmaceutically-acceptable carrier further comprises ethanol.

44. The article of manufacture of claim 41, wherein said acid is an organic acid.

45. The article of manufacture of claim 41, wherein said acid is a mineral acid.

46. The article of manufacture of claim 44, wherein said acid is acetic acid.

47. The article of manufacture of claim 44, wherein said acid is citric acid.

48. The article of manufacture of claim 47, wherein said citric acid is anhydrous.

49. The article of manufacture of claim 47, wherein said citric acid is monohydrous.

50. The article of manufacture of claim 47, wherein said citric acid is hydrous.

51. The article of manufacture of claim 42, wherein said acid is an organic acid.

52. The article of manufacture of claim 42, wherein said acid is a mineral acid.

53. The article of manufacture of claim 51, wherein said acid is acetic acid.

54. The article of manufacture of claim 51, wherein said acid is citric acid.

55. The article of manufacture of claim 54, wherein said citric acid is anhydrous.

56. The article of manufacture of claim 54, wherein said citric acid is monohydrous.

57. The article of manufacture of claim 54, wherein said citric acid is hydrous.

58. The article of manufacture of claim 43, wherein said acid is an organic acid.

59. The article of manufacture of claim 43, wherein said acid is a mineral acid.

60. The article of manufacture of claim 58, wherein said acid is acetic acid.

61. The article of manufacture of claim 58, wherein said acid is citric acid.

62. The article of manufacture of claim 61, wherein said citric acid is anhydrous.

63. The article of manufacture of claim 61, wherein said citric acid is monohydrous.

64. The article of manufacture of claim 61, wherein said citric acid is hydrous.

65. A pharmaceutical paclitaxel composition which is at least seven days old, comprising:
paclitaxel;
a pharmaceutically-acceptable carrier; and
an acid; said at least seven-day old composition being such that at least 96.6% of the original paclitaxel potency is retained when said composition is stored at 40° C. for seven days, and said at least seven-day old composition having at least 96.6% of its original paclitaxel potency.

66. A pharmaceutical paclitaxel composition according to claim 65, wherein said pharmaceutically-acceptable carrier comprises polyethoxylated castor oil.

67. A pharmaceutical paclitaxel composition of claim 66, wherein said pharmaceutically-acceptable carrier further comprises ethanol.

68. A pharmaceutical paclitaxel composition of claim 65, wherein said acid is an organic acid.

69. A pharmaceutical paclitaxel composition of claim 65, wherein said acid is a mineral acid.

70. A pharmaceutical paclitaxel composition of claim 68, wherein said acid is acetic acid.

71. A pharmaceutical paclitaxel composition of claim 68, wherein said acid is citric acid.

72. A pharmaceutical paclitaxel composition of claim 71, wherein said citric acid is anhydrous.

73. A pharmaceutical paclitaxel composition of claim 71, wherein said citric acid is monohydrous.

74. A pharmaceutical paclitaxel composition of claim 71, wherein said citric acid is hydrous.

75. A pharmaceutical paclitaxel composition of claim 66, wherein said acid is an organic acid.

76. A pharmaceutical paclitaxel composition of claim 66, wherein said acid is a mineral acid.

77. A pharmaceutical paclitaxel composition of claim 75, wherein said acid is acetic acid.

78. A pharmaceutical paclitaxel composition of claim 75, wherein said acid is citric acid.

79. A pharmaceutical paclitaxel composition of claim 78, wherein said citric acid is anhydrous.

80. A pharmaceutical paclitaxel composition of claim 78, wherein said citric acid is monohydrous.

81. A pharmaceutical paclitaxel composition of claim 78, wherein said citric acid is hydrous.

82. A pharmaceutical paclitaxel composition of claim 67, wherein said acid is an organic acid.

83. A pharmaceutical paclitaxel composition of claim 67, wherein said acid is a mineral acid.

84. A pharmaceutical paclitaxel composition of claim 82, wherein said acid is acetic acid.

85. A pharmaceutical paclitaxel composition of claim 82, wherein said acid is citric acid.

86. A pharmaceutical paclitaxel composition of claim 85, wherein said citric acid is anhydrous.

87. A pharmaceutical paclitaxel composition of claim 85, wherein said citric acid is monohydrous.

88. A pharmaceutical paclitaxel composition of claim 85, wherein said citric acid is hydrous.

89. A pharmaceutical paclitaxel composition which is at least seven days old, comprising:
paclitaxel;
a pharmaceutically-acceptable carrier; and
an acid; said at least seven-day old composition being such that the composition comprises no more than 2.3% total impurities when said composition is stored at 40° C. for seven days, and wherein said composition comprises no more than 2.3% total impurities.

90. A pharmaceutical paclitaxel composition according to claim 89, wherein said pharmaceutically-acceptable carrier comprises polyethoxylated castor oil.

91. A pharmaceutical paclitaxel composition of claim 90, wherein said pharmaceutically-acceptable carrier further comprises ethanol.

92. A pharmaceutical paclitaxel composition of claim 89, wherein said acid is an organic acid.

93. A pharmaceutical paclitaxel composition of claim 89, wherein said acid is a mineral acid.

94. A pharmaceutical paclitaxel composition of claim 92, wherein said acid is acetic acid.

95. A pharmaceutical paclitaxel composition of claim 92, wherein said acid is citric acid.

96. A pharmaceutical paclitaxel composition of claim 95, wherein said citric acid is anhydrous.

97. A pharmaceutical paclitaxel composition of claim 95, wherein said citric acid is monohydrous.

98. A pharmaceutical paclitaxel composition of claim 95, wherein said citric acid is hydrous.

99. A pharmaceutical paclitaxel composition of claim 90, wherein said acid is an organic acid.

100. A pharmaceutical paclitaxel composition of claim 90, wherein said acid is a mineral acid.

101. A pharmaceutical paclitaxel composition of claim 99, wherein said acid is acetic acid.

102. A pharmaceutical paclitaxel composition of claim 99, wherein said acid is citric acid.

103. A pharmaceutical paclitaxel composition of claim 102, wherein said citric acid is anhydrous.

104. A pharmaceutical paclitaxel composition of claim 102, wherein said citric acid is monohydrous.

105. A pharmaceutical paclitaxel composition of claim 102, wherein said citric acid is hydrous.

106. A pharmaceutical paclitaxel composition of claim 91, wherein said acid is an organic acid.

107. A pharmaceutical paclitaxel composition of claim 91, wherein said acid is a mineral acid.

108. A pharmaceutical paclitaxel composition of claim 106, wherein said acid is acetic acid.

109. A pharmaceutical paclitaxel composition of claim 106, wherein said acid is citric acid.

110. A pharmaceutical paclitaxel composition of claim 109, wherein said citric acid is anhydrous.

111. A pharmaceutical paclitaxel composition of claim 109, wherein said citric acid is monohydrous.

112. A pharmaceutical paclitaxel composition of claim 109, wherein said citric acid is hydrous.

113. An article of manufacture which is at least seven days old, comprising a sealed container and a pharmaceutical paclitaxel composition disposed within said sealed container, said composition comprising:
paclitaxel;
a pharmaceutically-acceptable carrier; and
an acid; said at least seven-day old composition being such that at least 96.6% of the original paclitaxel potency is retained when said composition is stored at 40° C. for seven days, and said at least seven-day old composition having at least 96.6% of its original paclitaxel potency.

114. An article of manufacture according to claim 113, wherein said pharmaceutically-acceptable carrier comprises polyethoxylated castor oil.

115. The article of manufacture according to claim 114, wherein said pharmaceutically-acceptable carrier further comprises ethanol.

116. An article of manufacture of claim 113, wherein said acid is an organic acid.

117. An article of manufacture of claim 113, wherein said acid is a mineral acid.

118. An article of manufacture of claim 116, wherein said acid is acetic acid.

119. An article of manufacture of claim 116, wherein said acid is citric acid.

120. An article of manufacture of claim 119, wherein said citric acid is anhydrous.

121. An article of manufacture of claim 119, wherein said citric acid is monohydrous.

122. An article of manufacture of claim 119, wherein said citric acid is hydrous.

123. An article of manufacture of claim 114, wherein said acid is an organic acid.

124. An article of manufacture of claim 114, wherein said acid is a mineral acid.

125. An article of manufacture of claim 123, wherein said acid is acetic acid.

126. An article of manufacture of claim 123, wherein said acid is citric acid.

127. An article of manufacture of claim 126, wherein said citric acid is anhydrous.

128. An article of manufacture of claim 126, wherein said citric acid is monohydrous.

129. An article of manufacture of claim 126, wherein said citric acid is hydrous.

130. An article of manufacture of claim 115, wherein said acid is an organic acid.

131. An article of manufacture of claim 115, wherein said acid is a mineral acid.

132. An article of manufacture of claim 130, wherein said acid is acetic acid.

133. An article of manufacture of claim 130, wherein said acid is citric acid.

134. An article of manufacture of claim 133, wherein said citric acid is anhydrous.

135. An article of manufacture of claim 133, wherein said citric acid is monohydrous.

136. An article of manufacture of claim 133, wherein said citric acid is hydrous.

137. An article of manufacture which is at least seven days old, comprising a sealed container and a pharmaceutical paclitaxel composition disposed within said sealed container, said composition comprising:

paclitaxel;

a pharmaceutically-acceptable carrier; and an acid; such that said composition comprises no more than 2.3% total impurities when stored at 40° C. for seven days, and wherein said composition comprises no more than 2.3% total impurities.

138. An article of manufacture according to claim 137, wherein said pharmaceutically-acceptable carrier comprises polyethoxylated castor oil.

139. The article of manufacture according to claim 138, wherein said pharmaceutically-acceptable carrier further comprises ethanol.

140. An article of manufacture of claim 137, wherein said acid is an organic acid.

141. An article of manufacture of claim 137, wherein said acid is a mineral acid.

142. An article of manufacture of claim 140, wherein said acid is acetic acid.

143. An article of manufacture of claim 140, wherein said acid is citric acid.

144. An article of manufacture of claim 143, wherein said citric acid is anhydrous.

145. An article of manufacture of claim 143, wherein said citric acid is monohydrous.

146. An article of manufacture of claim 143, wherein said citric acid is hydrous.

147. An article of manufacture of claim 138, wherein said acid is an organic acid.

148. An article of manufacture of claim 138, wherein said acid is a mineral acid.

149. An article of manufacture of claim 147, wherein said acid is acetic acid.

150. An article of manufacture of claim 147, wherein said acid is citric acid.

151. An article of manufacture of claim 150, wherein said citric acid is anhydrous.

152. An article of manufacture of claim 150, wherein said citric acid is monohydrous.

153. An article of manufacture of claim 150, wherein said citric acid is hydrous.

154. An article of manufacture of claim 139, wherein said acid is an organic acid.

155. An article of manufacture of claim 139, wherein said acid is a mineral acid.

156. An article of manufacture of claim 154, wherein said acid is acetic acid.

157. An article of manufacture of claim 154, wherein said acid is citric acid.

158. An article of manufacture of claim 157, wherein said citric acid is anhydrous.

159. An article of manufacture of claim 157, wherein said citric acid is monohydrous.

160. An article of manufacture of claim 157, wherein said citric acid is hydrous.

161. An article of manufacture produced by the process of:

(a) obtaining a sealable container;

(b) obtaining a pharmaceutical formulation comprising paclitaxel, a pharmaceutically-acceptable carrier, and an acid; said formulation being such that at least 96.6% of the paclitaxel potency is retained when the formulation is stored at 40° C. for seven days;

(c) placing said pharmaceutical formulation in said sealable container;

(d) sealing said sealable container; and (e) storing said pharmaceutical formulation in said sealed container for at least seven days;

wherein said pharmaceutical formulation retains at least 96.6% of the original paclitaxel potency.

162. The article of manufacture of claim 161, wherein said pharmaceutically-acceptable carrier comprises polyethoxylated castor oil.

163. The article of manufacture of claim 162, wherein said pharmaceutically-acceptable carrier further comprises ethanol.

164. The article of manufacture of claim 161, wherein said acid is an organic acid.

165. The article of manufacture of claim 161, wherein said acid is a mineral acid.

166. The article of manufacture of claim 164, wherein said acid is acetic acid.

167. The article of manufacture of claim 164, wherein said acid is citric acid.

168. The article of manufacture of claim 167, wherein said citric acid is anhydrous.

169. The article of manufacture of claim 167, wherein said citric acid is monohydrous.

170. The article of manufacture of claim 167, wherein said citric acid is hydrous.

171. The article of manufacture of claim 162, wherein said acid is an organic acid.

172. The article of manufacture of claim 162, wherein said acid is a mineral acid.

173. The article of manufacture of claim 171, wherein said acid is acetic acid.

174. The article of manufacture of claim 171, wherein said acid is citric acid.

175. The article of manufacture of claim 174, wherein said citric acid is anhydrous.

176. The article of manufacture of claim 174, wherein said citric acid is monohydrous.

177. The article of manufacture of claim 174, wherein said citric acid is hydrous.

178. The article of manufacture of claim 163, wherein said acid is an organic acid.

179. The article of manufacture of claim 163, wherein said acid is a mineral acid.

180. The article of manufacture of claim 178, wherein said acid is acetic acid.

181. The article of manufacture of claim 178, wherein said acid is citric acid.

182. The article of manufacture of claim 181, wherein said citric acid is anhydrous.

183. The article of manufacture of claim 181, wherein said citric acid is monohydrous.

184. The article of manufacture of claim 181, wherein said citric acid is hydrous.

185. An article of manufacture produced by the process of:

(a) obtaining a sealable container;

(b) obtaining a pharmaceutical formulation comprising paclitaxel, a pharmaceutically-acceptable carrier, and an acid; said formulation being such that the formulation comprises no more than 2.3% total impurities when said formulation is stored at 40° C. for seven days;

(c) placing said pharmaceutical formulation in said sealable container;

(d) sealing said sealable container; and (e) storing said pharmaceutical formulation in said sealed container for at least seven days;

wherein said formulation comprises not more than 2.3% total impurities.

186. The article of manufacture of claim 185, wherein said pharmaceutically-acceptable carrier comprises polyethoxylated castor oil.

187. The article of manufacture of claim 186, wherein said pharmaceutically-acceptable carrier further comprises ethanol.

188. The article of manufacture of claim 185, wherein said acid is an organic acid.

189. The article of manufacture of claim 185, wherein said acid is a mineral acid.

190. The article of manufacture of claim 188, wherein said acid is acetic acid.

191. The article of manufacture of claim 188, wherein said acid is citric acid.

192. The article of manufacture of claim 191, wherein said citric acid is anhydrous.

193. The article of manufacture of claim 191, wherein said citric acid is monohydrous.

194. The article of manufacture of claim 191, wherein said citric acid is hydrous.

195. The article of manufacture of claim 186, wherein said acid is an organic acid.

196. The article of manufacture of claim 186, wherein said acid is a mineral acid.

197. The article of manufacture of claim 195, wherein said acid is acetic acid.

198. The article of manufacture of claim 195, wherein said acid is citric acid.

199. The article of manufacture of claim 198, wherein said citric acid is anhydrous.

200. The article of manufacture of claim 198, wherein said citric acid is monohydrous.

201. The article of manufacture of claim 198, wherein said citric acid is hydrous.

202. The article of manufacture of claim 187, wherein said acid is an organic acid.

203. The article of manufacture of claim 187, wherein said acid is a mineral acid.

204. The article of manufacture of claim 202, wherein said acid is acetic acid.

205. The article of manufacture of claim 202, wherein said acid is citric acid.

206. The article of manufacture of claim 205, wherein said citric acid is anhydrous.

207. The article of manufacture of claim 205, wherein said citric acid is monohydrous.

208. The article of manufacture of claim 205, wherein said citric acid is hydrous.

209. A pharmaceutical paclitaxel composition having improved stability comprising: paclitaxel;
  polyethoxylated castor oil; and
  an acid;
  said acid improving the stability of the paclitaxel as compared to an identical composition without said acid; and
  wherein said acid-containing paclitaxel composition is such that at least 97.5% of the paclitaxel potency is retained when the composition is stored at 40° C. for 7 days.

210. The pharmaceutical paclitaxel composition of claim 209, further comprising ethanol.

211. The pharmaceutical paclitaxel composition of claim 209, wherein said acid is an organic acid.

212. The pharmaceutical paclitaxel composition of claim 209, wherein said acid is a mineral acid.

213. The pharmaceutical paclitaxel composition of claim 211, wherein said acid is citric acid.

214. The pharmaceutical paclitaxel composition of claim 213, wherein said citric acid is monohydrous.

215. The pharmaceutical paclitaxel composition of claim 213, wherein the citric acid is hydrous.

216. The pharmaceutical paclitaxel composition of claim 213, wherein the citric acid is anhydrous.

217. The pharmaceutical paclitaxel composition of claim 211, wherein said acid is acetic acid.

218. The pharmaceutical paclitaxel composition of claim 210, wherein said acid is an organic acid.

219. The pharmaceutical paclitaxel composition of claim 210, wherein said acid is a mineral acid.

220. The pharmaceutical paclitaxel composition of claim 218, wherein said acid is citric acid.

221. The pharmaceutical paclitaxel composition of claim 220, wherein said citric acid is monohydrous.

222. The pharmaceutical paclitaxel composition of claim 220, wherein the citric acid is hydrous.

223. The pharmaceutical paclitaxel composition of claim 220, wherein the citric acid is anhydrous.

224. The pharmaceutical paclitaxel composition of claim 218, wherein said acid is acetic acid.

225. An improved pharmaceutical paclitaxel composition, said composition comprising as ingredients paclitaxel;
  polyethoxylated castor oil; and ethanol;
  the improvement comprising an acid mixed with said ingredients such that the stability of the paclitaxel composition is improved as compared to the same paclitaxel composition without said acid; and
  said improved paclitaxel composition being such that at least 97.5% of the paclitaxel potency is retained when said composition is stored at 40° C. for 7 days.

226. The improved pharmaceutical paclitaxel composition of claim 225, said composition being substantially free of water.

227. The improved pharmaceutical paclitaxel composition of claim 226, wherein said acid is an organic acid.

228. The improved pharmaceutical paclitaxel composition of claim 226, wherein said acid is a mineral acid.

229. The improved pharmaceutical paclitaxel composition of claim 227, wherein said acid is citric acid.

230. The improved pharmaceutical paclitaxel composition of claim 229, wherein said citric acid is monohydrous.

231. The improved pharmaceutical paclitaxel composition of claim 229, wherein the citric acid is hydrous.

232. The improved pharmaceutical paclitaxel composition of claim 229, wherein the citric acid is anhydrous.

233. The improved pharmaceutical paclitaxel composition of claim 227, wherein said acid is acetic acid.

234. A pharmaceutical paclitaxel composition consisting essentially of:
  paclitaxel;
  polyethoxylated castor oil;
  ethanol; and
  an acid;
  said acid being in sufficient amount to confer improved paclitaxel stability to said composition as compared to the paclitaxel stability in the same composition without said acid; said
  pharmaceutical paclitaxel composition being substantially free of water; and
  said composition being such that at least 97.5% of the paclitaxel potency is retained when said composition is stored at 40° C. for 7 days.

235. The pharmaceutical paclitaxel composition of claim 234, wherein said acid is an organic acid.

236. The pharmaceutical paclitaxel composition of claim 234, wherein said acid is a mineral acid.

237. The pharmaceutical paclitaxel composition of claim 235, wherein said acid is citric acid.

238. The pharmaceutical paclitaxel composition of claim 237, wherein said citric acid is monohydrous.

239. The pharmaceutical paclitaxel composition of claim 237, wherein the citric acid is hydrous.

240. The pharmaceutical paclitaxel composition of claim 237, wherein the citric acid is anhydrous.

241. The pharmaceutical paclitaxel composition of claim 236, wherein said acid is acetic acid.

242. An article of manufacture comprising a sealed container and a pharmaceutical paclitaxel composition disposed within said sealed container, said pharmaceutical paclitaxel composition being substantially free of water and comprising:

paclitaxel;

polyethoxylated castor oil;

ethanol; and an acid;

said acid being in sufficient amount to confer improved paclitaxel stability to said composition as compared to the same composition without said acid; and said composition being such that at least 97.5% of the paclitaxel potency is retained when said composition is stored at 40° C. for seven days.

243. The article of manufacture of claim 242, wherein said acid is an organic acid.

244. The article of manufacture of claim 242, wherein said acid is a mineral acid.

245. The article of manufacture of claim 243, wherein said acid is acetic acid.

246. The article of manufacture of claim 243, wherein said acid is citric acid.

247. The article of manufacture of claim 246, wherein said citric acid is anhydrous.

248. The article of manufacture of claim 246, wherein said citric acid is monohydrous.

249. The article of manufacture of claim 246, wherein said citric acid is hydrous.

250. An article of manufacture produced by the process of:

(a) obtaining a sealable container;

(b) obtaining a pharmaceutical formulation consisting essentially of paclitaxel, polyethoxylated castor oil, ethanol, and an acid; said acid being in sufficient amount such that the paclitaxel stability in said formulation is improved as compared to the stability of paclitaxel in the same formulation without said acid, and said acid-containing formulation being such that at least 97.5% of the paclitaxel potency is retained when said formulation is stored at 40° C. for seven days;

(c) placing said pharmaceutical formulation in said sealable container;

(d) sealing said sealable container; and (e) storing said pharmaceutical formulation in said sealed container for at least seven days.

251. The article of manufacture of claim 250, wherein said acid is an organic acid.

252. The article of manufacture of claim 250, wherein said acid is a mineral acid.

253. The article of manufacture of claim 251, wherein said acid is acetic acid.

254. The article of manufacture of claim 251, wherein said acid is citric acid.

255. The article of manufacture of claim 254, wherein said citric acid is anhydrous.

256. The article of manufacture of claim 254, wherein said citric acid is monohydrous.

257. The article of manufacture of claim 254, wherein said citric acid is hydrous.

258. A pharmaceutical paclitaxel composition which is at least 7 days old, consisting essentially of:

paclitaxel;

polyethoxylated castor oil;

ethanol; and an acid;

said acid being in sufficient amount such that the paclitaxel stability of said composition is improved as compared to the paclitaxel stability of an identical composition without said acid; and said at least 7-day-old composition being such that at least 97.5% of the original paclitaxel potency is retained.

259. A pharmaceutical paclitaxel composition of claim 258, wherein said acid is an organic acid.

260. A pharmaceutical paclitaxel composition of claim 258, wherein said acid is a mineral acid.

261. A pharmaceutical paclitaxel composition of claim 259, wherein said acid is acetic acid.

262. A pharmaceutical paclitaxel composition of claim 259, wherein said acid is citric acid.

263. A pharmaceutical paclitaxel composition of claim 262, wherein said citric acid is anhydrous.

264. A pharmaceutical paclitaxel composition of claim 262, wherein said citric acid is monohydrous.

265. A pharmaceutical paclitaxel composition of claim 262, wherein said citric acid is hydrous.

* * * * *